(12) United States Patent
Wroblesky et al.

(10) Patent No.: US 10,150,884 B2
(45) Date of Patent: Dec. 11, 2018

(54) COMPOSITION, METHODS AND DEVICES USEFUL FOR MANUFACTURING OF IMPLANTABLE ARTICLES

(71) Applicant: SECANT MEDICAL, INC., Telford, PA (US)

(72) Inventors: Kayla Wroblesky, Freehold, NJ (US); Peter D. Gabriele, Perkasie, PA (US); Jeremy J. Harris, Doylestown, PA (US); Carissa Smoot, Sellersville, PA (US); Charles Brendan Nicholson, Quakertown, PA (US); Austin Robertson, Sellersville, PA (US); Julia Donnelly, Chalfont, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 471 days.

(21) Appl. No.: 14/826,865

(22) Filed: Aug. 14, 2015

(65) Prior Publication Data

US 2016/0046832 A1 Feb. 18, 2016

Related U.S. Application Data

(60) Provisional application No. 62/037,640, filed on Aug. 15, 2014, provisional application No. 62/037,425, filed on Aug. 14, 2014.

(51) Int. Cl.
| | |
|---|---|
| C09D 167/00 | (2006.01) |
| C08L 89/00 | (2006.01) |
| C09D 189/00 | (2006.01) |
| A61L 27/18 | (2006.01) |
| A61L 27/22 | (2006.01) |

(Continued)

(52) U.S. Cl.
CPC ............ *C09D 167/00* (2013.01); *A61L 27/18* (2013.01); *A61L 27/222* (2013.01); *A61L 27/24* (2013.01); *A61L 27/56* (2013.01); *C09D 189/00* (2013.01); *B33Y 10/00* (2014.12); *B33Y 70/00* (2014.12)

(58) Field of Classification Search
None
See application file for complete search history.

(56) References Cited

U.S. PATENT DOCUMENTS 5,863,551 A * 1/1999 Woerly ................... A61L 27/26
424/423
6,017,566 A 1/2000 Bunczek et al.
(Continued)

OTHER PUBLICATIONS

Sun, ZJ et. al., Materials Science and Engineering, The influence of lactic acid on the properties of Poly (glycerol-sebacate-lactic acid),2009, p. 178-182, C29.

(Continued)

*Primary Examiner* — Jacob T Minskey
*Assistant Examiner* — Baileigh Kate Darnell
(74) *Attorney, Agent, or Firm* — McNees Wallace & Nurick LLC

(57) ABSTRACT

The application is directed to aqueous dispersible biodegradable compositions of esters which are the condensation reaction product of a polyol and a diacid which are within a matrix of hydrated polypeptide. The compositions are useful in additive manufacturing and other applications for use with implantable articles. In some embodiments, the ester in the compositions is the product of a glyercol-sebacic acid condensation reaction.

18 Claims, 12 Drawing Sheets

(51) Int. Cl.
    A61L 27/24    (2006.01)
    A61L 27/56    (2006.01)
    B33Y 10/00    (2015.01)
    B33Y 70/00    (2015.01)

(56)         References Cited

U.S. PATENT DOCUMENTS

| | | | |
|---|---|---|---|
| 6,444,782 | B1 | 9/2002 | Hamlin |
| 7,722,894 | B2 | 5/2010 | Wang et al. |
| 7,745,562 | B2 * | 6/2010 | Rosing .................. C09J 167/00 424/443 |
| 8,143,042 | B2 * | 3/2012 | Bettinger ................ A61L 27/18 424/423 |
| 8,716,410 | B2 | 5/2014 | Venkatraman et al. |
| 8,912,304 | B2 * | 12/2014 | Bruggeman ............ A61L 27/16 525/418 |
| 9,492,400 | B2 * | 11/2016 | Jon ....................... A61K 9/5192 |
| 9,731,046 | B2 * | 8/2017 | Cohen .................... A61K 38/18 |
| 2003/0055506 | A1 * | 3/2003 | Stoy ......................... A61F 2/441 623/17.16 |
| 2003/0118692 | A1 | 6/2003 | Wang et al. |
| 2004/0151705 | A1 * | 8/2004 | Mizuno .................. A61L 27/24 424/93.7 |
| 2006/0009839 | A1 | 1/2006 | Tan |
| 2008/0262102 | A1 * | 10/2008 | Wang .................... A61L 24/046 514/772.5 |
| 2009/0214373 | A1 | 8/2009 | Stinson et al. |
| 2011/0212501 | A1 * | 9/2011 | Yoo ......................... A61L 27/54 435/174 |
| 2012/0143347 | A1 | 6/2012 | Wang et al. |

OTHER PUBLICATIONS

Wang, Yadong et. al. A Tough Biodegradable Elastomer, vol. 20, p. 602-606, Jun. 2002, Nature Publishing Group.

Gao, Jin et. al., Macroporous Elastomeric Scaffolds with Extensive Micropores for Soft Tissue Engineering, Wallace H. Coulter Department of Biomedical Engineering, Georgia Institute of Technology, vol. 12, p. 917-925, Feb. 4, 2010, Mary Ann Liebert, Inc.

Jaafar, Israd et. al., Spectroscopic evaluation, thermal, and thermomechanical characterization of poly(glycerol-sebacate) with variations in curing temperatures and durations, J. Mater Sci, p. 2525-2529, Sep. 13, 2009, Springer Science+Business Media, LLC.

Pryor, Howard et. al., Poly(glycerol sebacate) films prevent postoperative adhesions and allow laparoscopic placement, Surgery, vol. 146, No. 3, p. 490-497, 2009, Boston, MA.

Guo, Xiao-Long et. al., Characterization and optimization of glycerol/sebacate ratio in poly(glycerol-sebacate) elastomer for cell culture application, J. Biomed Mater Res Part A, vol. 102A, Issue 11, p. 3903-3907, Nov. 2014, Society for Biomaterials.

Chen, Qi-Zhi et. al., Characterisation of a soft elastomer poly(glycerol sebacate) designed to match the mechanical properties of myocardial tissue, ScienceDirect, p. 47-57, 2008, Biomaterials.

* cited by examiner

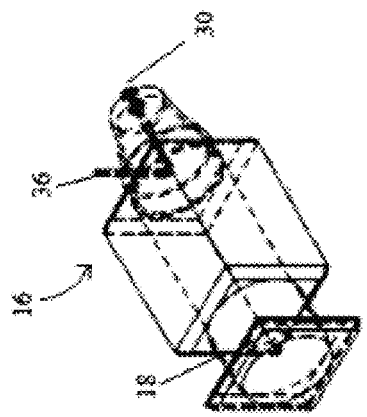
FIG. 4C
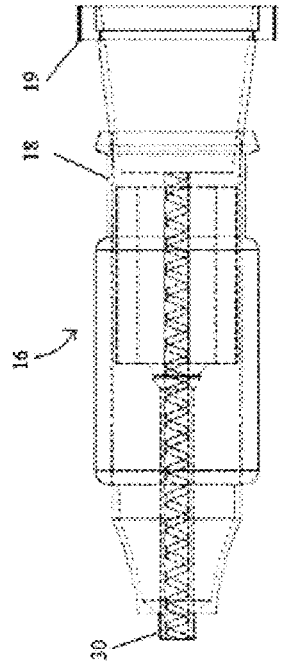
FIG. 4E
FIG. 4B
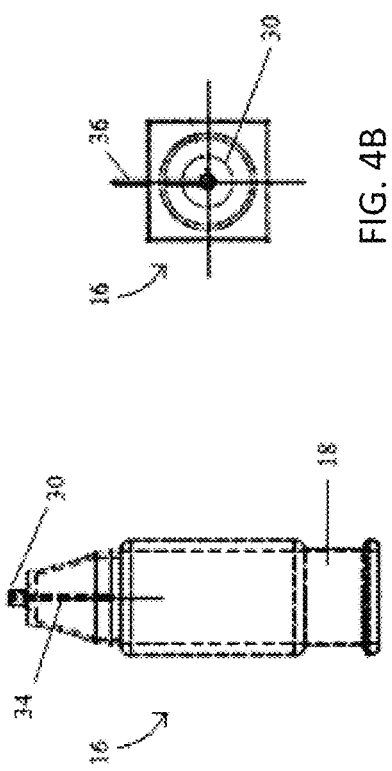
FIG. 4A
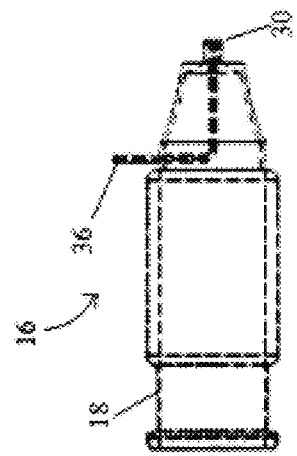
FIG. 4D

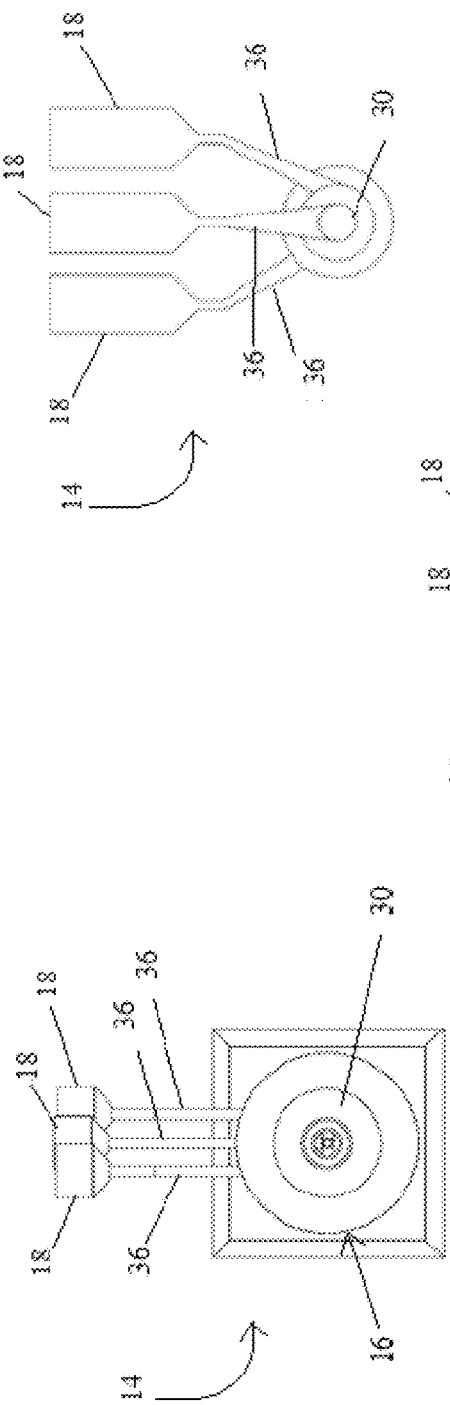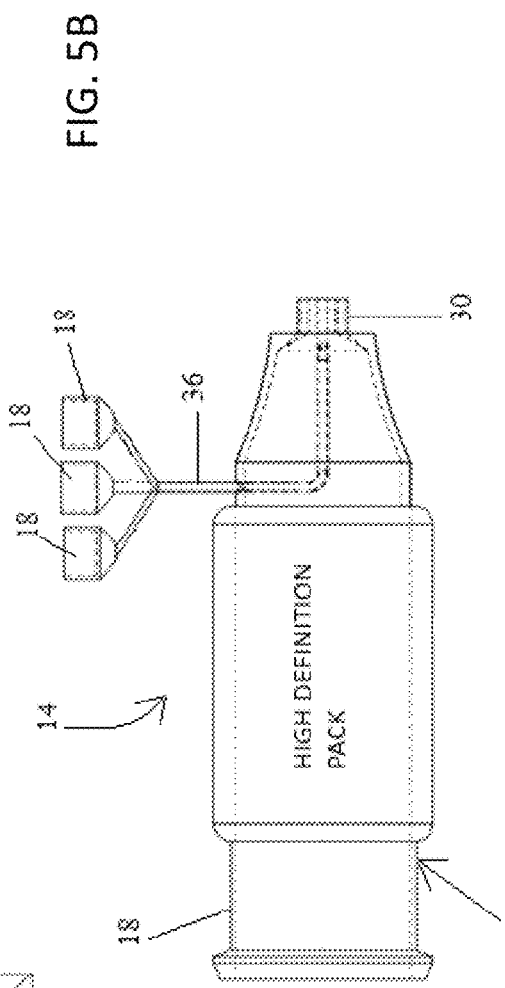
FIG. 5A
FIG. 5B
FIG. 5C

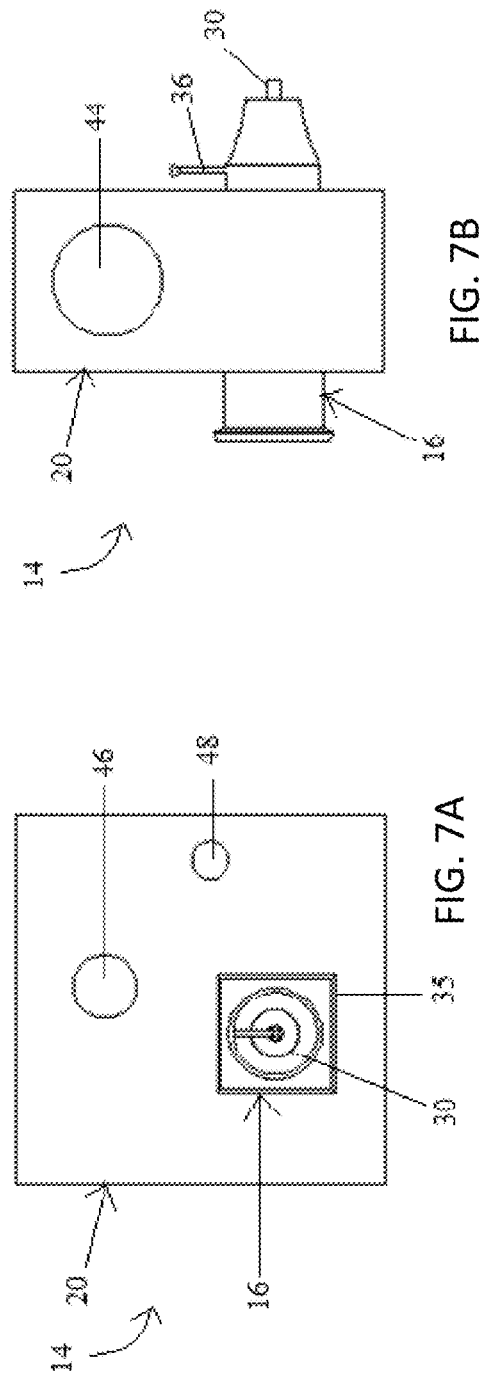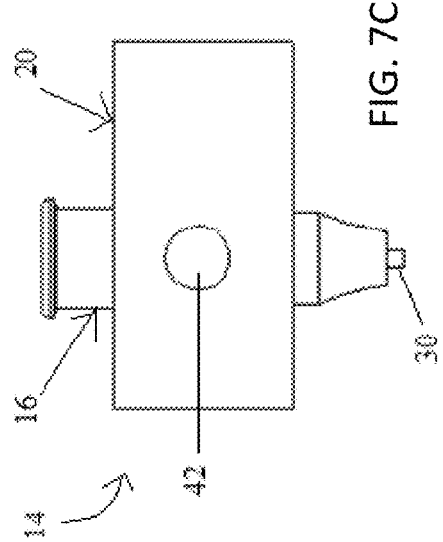

COMPOSITION, METHODS AND DEVICES USEFUL FOR MANUFACTURING OF IMPLANTABLE ARTICLES

CROSS-REFERENCE TO RELATED APPLICATIONS

This application claims the benefit of, and priority to, U.S. App. Nos. 62/037,425 filed Aug. 14, 2014 and 62/037,640 filed Aug. 15, 2014 both of which are hereby incorporated by reference in their entirety.

FIELD

This application relates to the field of material science and materials useful in the manufacture of implantable articles, such as additive manufacturing. More specifically, the present invention provides an aqueous dispersible biodegradable composition of esters formed from a polyol/diacid condensation reaction within a matrix of hydrated polypeptide.

BACKGROUND

A number of pressing problems confront the healthcare industry. As of June 2012 the United Network for Organ Sharing (UNOS) had 114,636 patients registered as needing an organ transplant. According to UNOS, between January and March 2012 only 6,838 transplants were performed. Each year more patients are added to the UNOS list than transplants are performed, resulting in a net increase in the number of patients waiting for a transplant.

This has placed an economic burden on the US healthcare economy both in direct and indirect costs. Organ transplant and regenerative medicine are expected to eventually meet the challenge of replacement and regeneration as the portfolio of biomaterials increases. In the past 50 years, scientists have been limited in the choice of biomaterials useful in tissue/organ engineering.

One new biomaterial, poly(glycerol sebacate), was developed for tissue engineering and has expanded into therapeutic areas including drug delivery, orthopedics, cardiovascular, neurovascular and soft tissue repair. With benefits such as little to no fibrous capsule formation, antimicrobial activity, non-immunogenicity, among others, the material is desirable for implantable as well as topical applications. Current forms of this biomaterial, however, have some limitations on its ability to be manipulated into various forms for specific applications.

Additive manufacturing has become an important tissue scaffold fabrication tool in tissue engineering and regenerative medicine. Precise patient specific 3-D tissue scaffold constructs when designed by software imported from such 3-D medical diagnostic imaging modalities as MRI and ultrasound, can reconstruct in vitro and in vivo tissue framework (tissue scaffold) from subject tissue.

There is a serious limitation to the choice of biocompatible and resorbable polymer technologies to build the basic compositions supporting scaffold structures by additive manufacturing. Historically, lactide and glycolide polymers have been the resorbable polymers of choice. While the basic chemistry is resorbable, the question of biocompatibility has been challenged. Once in the wound space, lactide and glycolide polymers break down, releasing highly acidic by-products which extend the healing period, adversely impact the immune system, and form scar tissue, disrupting the return of native function.

SUMMARY

Exemplary embodiments are directed to aqueous dispersible biodegradable compositions of esters which are the condensation reaction products of a polyol and a diacid and are within a matrix of hydrated polypeptide, as well as to articles made therefrom and methods and devices which employ those compositions.

According to an exemplary embodiment, a composition comprises water, an ester of a polyol and a diacid and a polypeptide. In some embodiments, the ester comprises a glyercol-sebacic acid ester compound, such as a polymeric glyercol-sebacic acid ester compound.

According to another embodiment, a method for forming a composition comprises mixing a solid polypeptide in water to form a polypeptide hydrogel and adding a glyercol-sebacic acid ester compound to the polypeptide hydrogel.

According to another embodiment, a method for printing a three-dimensional article comprises extruding a first two-dimensional layer of the compositions described herein onto a substrate and building a second two-dimensional layer of that composition upon the first layer.

According to yet another embodiment, a method for forming an article comprises extruding a fiber of the compositions described herein, which in some embodiments involves co-extrusion with one or more other polymeric compositions in forming the fiber.

According to still another embodiment, a print head for use in additive manufacturing comprises a nozzle and a plurality of reservoirs, each reservoir containing a biocompatible material, the nozzle comprising a tip in fluid communication with each of the reservoirs via a feed line, the nozzle having a pitched bore to accomplish mixing of the biocompatible materials during extrusion.

Among the advantages of exemplary embodiments is that compositions are provided that can overcome many of the limitations of conventional materials used in implantable articles, such as limiting scarring and providing a compliance modulus that better approximates native tissue.

Another advantage is that compositions are provided for use in formation of implantable materials that can result in regeneration of tissue in the absence of exogenous factors like stem cells, mesenchymal cells, trophic agents or other biologics.

Still another advantage is that compositions are provided that accomplish biological benefits associated with its constituents in a form suitable for use in a variety of processes including additive manufacturing, molding, coating, forming techniques, machining and extrusion.

Other features and advantages of the present invention will be apparent from the following more detailed description of exemplary embodiments that illustrate, by way of example, the principles of the invention.

BRIEF DESCRIPTION OF THE DRAWINGS

The following detailed description of exemplary embodiments may be better understood when read in conjunction with the appended drawings. It should be understood, however, that the invention is not limited to the precise arrangements and instrumentalities shown.

FIG. 4A is a top plan view of a nozzle according to an exemplary embodiment of the invention;

FIG. 4B is a rear elevational view of the nozzle shown in FIG. 4A;

FIG. 4C is a perspective view of the nozzle shown in FIG. 4A;

FIG. 4D is a side view of the nozzle shown in FIG. 4A;

FIG. 4E is a nozzle in accordance with another embodiment;

FIG. 5A is a front cross sectional view of a nozzle according an exemplary embodiment of to the invention;

FIG. 5B is a front cross sectional view of the feedline assembly of the nozzle shown in FIG. 5A;

FIG. 5C is a side view of the nozzle shown in FIG. 5A;

FIG. 7A is a bottom elevational view of the heating element shown in FIG. 6A assembled together with the nozzle shown in FIG. 4A;

FIG. 7B is a side elevation view of the heating element shown in FIG. 6A assembled together with the nozzle shown in FIG. 4A; and FIG. 7C is another side view of the heating element shown in FIG. 6A assembled together with the nozzle shown in FIG. 4A.

DETAILED DESCRIPTION OF EXEMPLARY EMBODIMENTS

Exemplary embodiments are directed to aqueous dispersible biodegradable compositions of esters which are the condensation reaction product of a polyol and a diacid (such as glycerol and sebacic acid) which are within a matrix of hydrated polypeptide. Exemplary embodiments also relate to articles made from, and methods and devices which employ, those compositions, such as in additive manufacturing processes which are also sometimes referred to as 3-D printing.

While compositions and other embodiments herein are primarily discussed with respect to additive manufacturing processes, the invention is not so limited and the compositions may be employed for any other suitable application, including molding, coating, forming techniques, machining or extrusion.

Bio-printing, such as of organs, tissues and other structures to be implanted into the body, is a convergent technology of 3-D stereo lithography, ink jet printing, tissue engineering, polymer chemistry and tissue-cell biology. The basic concept of 3-D organ printing in tissue engineering is to reproduce tissue, or tissue constructs, through the use of formulations with cellular incorporation or the creation of freestanding scaffolds upon which cells can grow into organs.

3-D printing generally, also known as additive manufacturing, is where successive layers of material are laid down under computer control in an x-y plane to build the object layer by layer in the z-direction. The print-head nozzle can be an extrusion apparatus that deposits each layer of material in a 2-D horizontal plane like a common ink-jet printer.

A 3-D object can be sliced up into a finite number of horizontal planes. Reassembling these planes in the vertical direction recreates the object. 3-D printing reassembles these planes to recreate the object. In embodiments of the invention, instead of "ink" that is traditionally used in 3-D printing, the 3-D print head nozzle extrudes a biocompatible and/or bioresorbable polymer. Once a bioresorbable polymer composition has been deposited in a 2-D layer the print-head or platform stage indexes up or down (i.e., in the z-direction) wherein, the next 2-D layer is printed on the previous layer to rebuild the full structure.

Figure 1:
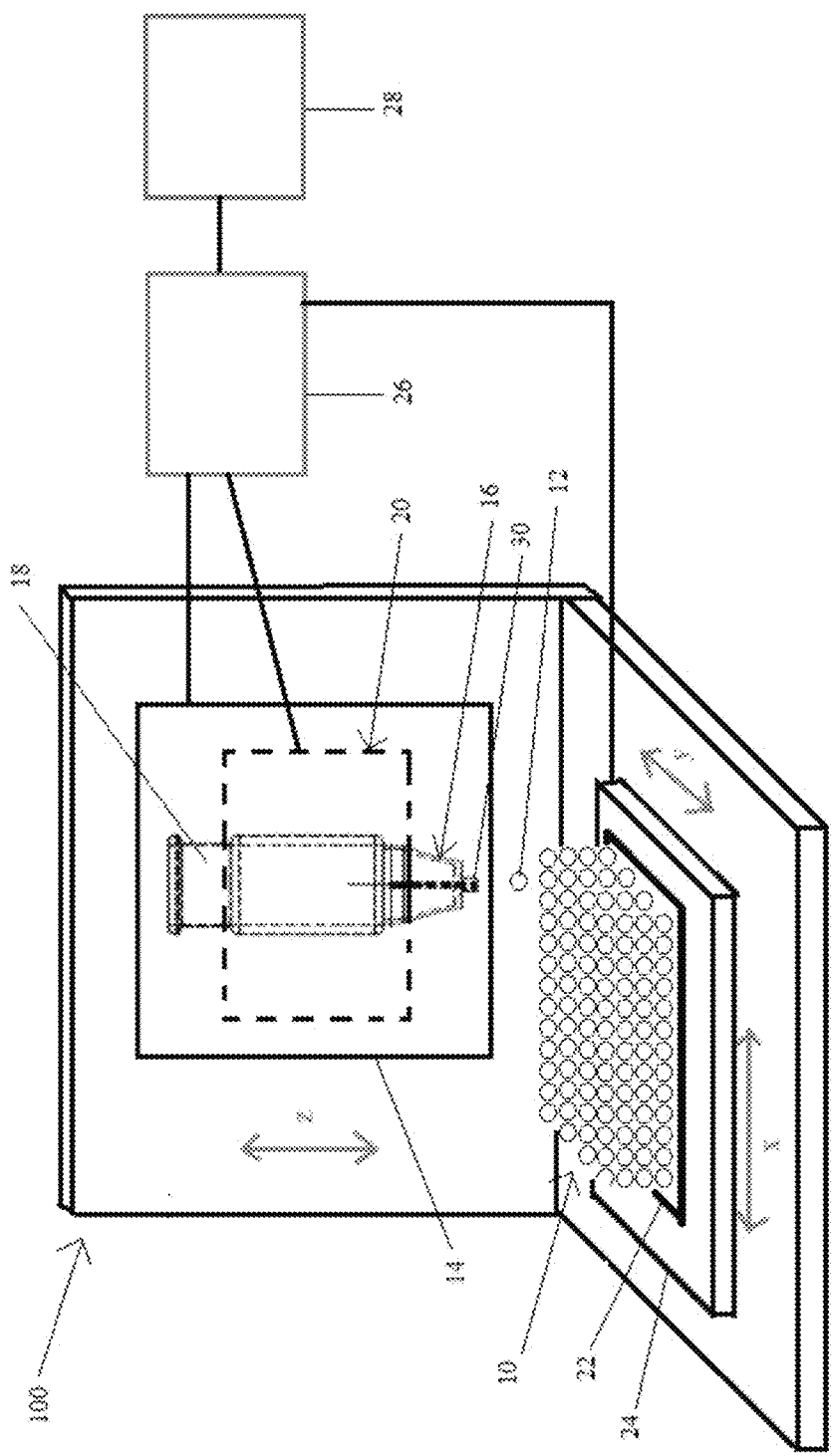
FIG. 1 is a 3-D printer assembly system in accordance with an exemplary embodiment.

Referring to FIG. 1, a 3-D printed object 10 is printed from a composition 12. A 3-D printer assembly 100 includes a print head 14 and a platform 24. The print head 14 includes a nozzle 16 and a reservoir 18 for holding composition 12. Print head 14 optionally further comprises a heating element 20. To print the 3-D printed object, the composition 12 may be, in some embodiments, heated by the heating element 20, extruded from reservoir 18 through tip 30 and deposited onto a substrate 22 to form a layer in the xy direction. The nozzle 16 and/or platform 24 may be moved in the x, y, and z directions to enable deposition of successive xy layers, building the object 10 in the z direction. In some embodiments the 3-D printer assembly 100 further comprises a computer 26. Computer 26 may be programmed to control movement of the nozzle 16 and/or platform 24 as well as temperature of the heating element 20 and/or platform 24.

While shown in FIG. 1 as being printed as discrete elements, it will be appreciated that a variety of manufacturing methods are contemplated herein. In some embodiments, the composition 12 is extruded through the nozzle 16 in a continuous manner to form a fiber that can be used in directly forming an article or wound for the production of yarn and subsequent formation of textiles.

The composition 12 is a formulation of a bioresorbable polymer and polypeptides and generally comprises water, a polypeptide, and a condensation polymer of a polyol and a diacid, such as a glycerol-sebacic acid ester compound, for example. In some embodiments, the composition 12 includes one or more of the bioresorbable biocompatible materials based on metabolite building blocks disclosed in U.S. Pat. No. 7,722,894, which is hereby incorporated by reference in its entirety.

The glycerol-sebacic acid ester compound may be present in polymeric form, having a molecular weight greater than 10,000 (also referred to herein as PGS); having a molecular weight of 10,000 or less, which may considered an oligomeric form (also referred to herein as OGS); or some combination of high and low molecular weight forms of the ester.

The use of PGS and OGS can overcome many of the limitations of lactides and glycolides including exclusion of scarring. PGS is a bioelastomer, whereas the lactides and glycolides are rigid thermoplastic bioresorbable polymers. Additionally, the bioelastomeric feature provides healing tissue with the appropriate compliance modulus that encourages a scaffold environment more like native tissue. A physiologically compliant scaffold modulus emulates the extracellular matrix (ECM) enhancing pro-healing cell signaling.

In some embodiments, the PGS of the composition 12 hydrolyzes (breaks down) into cellular metabolites that may be consumed by the Krebs cycle, whereas the lactides and glycolides must be removed from the body by non-metabolic processes. Without being bound by theory, when PGS is used as an in vivo tissue scaffold, it may attract native tissue stem cells without the aid of exogenous trophic agents or progenitor cells.

In some embodiments, the composition 12 consists solely of water, polypeptide, and glycerol-sebacic acid ester compound to the exclusion of cells, biologics, trophic agents, growth agents, or other bioactive compounds. Among the advantages of exemplary embodiments are that regeneration of tissue may be accomplished in the absence of exogenous factors like stem cells, mesenchymal cells, trophic agents or other biologics and that composition 12 may promote endogenous regeneration. It will be appreciated however, that such compounds are not excluded from composition 12 in all cases and that other embodiments may employ one or more bioactives.

Without wishing to be bound by theory, it is believed that in embodiments which employ PGS in the composition 12, the composition's breakdown/erosion mechanism is as a surface eroder, which contrasts with more conventional materials such as lactides and glycolides, which are bulk eroders. Surface erosion is attractive to both controlled degradation of the biopolymer as a matrix scaffold material and as a matrix material for controlled drug or biologic release. Accordingly, the degradation mechanism will not lead to premature scaffold weakening.

In some embodiments, the composition 12 is prepared as a single uniform aqueous phase and is free of dispersing agents.

The composition 12 may be processed at extrusion temperatures compatible with living cells or described as "cold" extrusion, being in the range of about 35° C. to about 40° C. in some embodiments, which is a relative term with respect to generally higher polymer melt or flow temperatures (e.g. greater than about 200° C., for example). An improved "cold" extrusion nozzle 16 is provided which raises the nozzle temperature slightly within body temperature range in order to increase the potential for a higher solids polymer flow as well as form a smoother extrudate.

By the nature of 3-D printing, the material extruded must be able to flow through a nozzle as well as stick to the build platform or below layer in order to create an object. In typical Fused Filament Fabrication (FFF), this is done by melting the polymer (e.g. for acrylonitrile butadiene styrene (ABS), at 230° C.) and then setting the build platform to the glass transition temperature (e.g. for ABS 110° C.). At this low temperature extrusion, the material used for printing should be able to can flow but still set up in a relatively short time frame. The composition in accordance with certain exemplary embodiments can set up in less than 2 minutes.

Current bioprinter inks that utilize cold extrusion have limited strength and adhesion to previous layers without cellular culture. Cells are commonly suspended within the matrix and eventually grow and replace the matrix. As noted, however, compositions used in accordance with exemplary embodiments does not require the use of cells, but has the ability to include them due to the low melt flow temperatures.

The composition, although referenced as a bio-ink in relation to certain exemplary embodiments, need not be liquid in every case and may also be semi-solid or solid.

In some embodiments, the present invention provides compositions of specific materials of construction that promote cell proliferation in the absence of any trophic agent using a base polymer poly (glycerol-sebacate) (PGS) as a bulk vehicle that may be co-modified with OGS, which can aid as a plasticizer, dispersing agent, wetting agent, processing aid or resin stabilizer.

In some embodiments of composition 12, various glycerol-sebacic acid esters and collagen and its derivatives as formulation modifiers are utilized. An advantage of this composition is uniformity of polymer composition, extrusion at physiological temperatures, and instantaneous solidification resulting in a fully bioresorbable polymer tissue scaffold that is comprised of biocompatible materials. It is a further advantage of this composition that it is comprised of natural metabolites to accomplish formulating chemistry requirements.

The present invention may include a composition of matter 12 used as 3-D scaffold building material, a.k.a. "bio-ink," providing bioresorbable properties with or without specific biological cells or trophic components thereof, capable of being spatially deposited through a 3-D print nozzle 16 at physiological temperatures. The composition 12 may be formulated to go through a cold extrusion, via a syringe and plunger system, material reservoir and pneumatic system or other extrusion through an orifice without the addition of heat. In one embodiment, the present invention provides composition 12 comprising water, a polypeptide, and a condensation polymer of a polyol and a diacid. In another embodiment, the composition 12 further comprises condensation oligomer of a polyol and a diacid. In another embodiment, a composition 12 of the invention further comprises a bioactive material. In another embodiment of this invention condensation polymer and/or oligomer of the composition 12 can be functionalized to provide cross-linkable chemistry in the post print structure (i.e. the structure formed by printing and before further processing, also referred to as the "A stage" structure). Such functional groups may be induced to cause cross-linking, for example by heating or photocuring the A stage structure, to provide for post print stability (resulting in what may be referred to as a "B stage" structure).

As discussed previously, in some embodiments composition 12 comprises water; polypeptide, and an ester compound that is the condensation reaction product of a polyol and a diacid, preferably of glycerol and sebacic acid. In some embodiments, the polymeric glycerol-sebacic acid ester and/or oligomeric glycerol-sebacic acid ester may be functionalized. In some embodiments the polypeptide is collagen or gelatin. The relative amounts of the components of composition 12 may be adjusted to fine tune the physical properties of composition 12 and/or the 3-D solid 10 built from composition 12.

In one embodiment, a composition in accordance with an exemplary embodiment comprises
    about 30% to about 85% by weight water;
    about 10% to about 60% by weight glycerol-sebacic acid ester compound; and
    about 0.1% to about 30% by weight polypeptide.
In another embodiment, the composition comprises
    about 40% to about 85% by weight water;
    about 10% to about 50% by weight glycerol-sebacic acid ester compound; and
    about 5% to about 30% by weight polypeptide.

It will be appreciated that the specific amounts and ranges of amounts may depend somewhat on the application for which the composition is employed, with lesser amounts of polypeptide presently preferred for fiber applications.

In some embodiments the water component is present in a range of about 35% to about 85% by weight. In some embodiments the water component is present in a range of from about 40% to about 80% by weight; such as about 50% to about 75% by weight. In some embodiments the composition 12 comprises about 40%, about 45%, about 50%, about 55%, about 60%, about 65%, about 70%, about 75%, about 80%, or about 85% by weight water or any number, range or sub-range between any of the foregoing.

In some embodiments the glycerol-sebacic acid ester compound is present as from about 10% to about 60% by weight, such as about 10%, about 15%, about 20%, about 25%, about 30%, about 35%, about 40%, about 45%, about 50%, about 55%, or about 60% by weight, or any number, range or sub-range between any of the foregoing. The glycerol-sebacic acid ester compound may be present as PGS, OGS, or as a combination of the two.

In some embodiments the polypeptide component is present in a range of about 0.1% to about 30% by weight. In some embodiments, composition 12 comprises about 0.5%, about 1%, about 5%, about 10%, about 15%, about 20%, about 25%, or about 30%, by weight polypeptide as well as any number, range or sub-range between any of the foregoing.

In some embodiments, composition 12 comprises total solids in a range of about 15% to about 65% by weight.

In accordance with the present invention, poly-, polymer, and polymeric refer to intermediate weight polymers formed by esterification of a polyol and a diacid, oligo-, oligomer, and oligomeric refer to low molecular weight polymers formed by esterification of a polyol and a diacid, and thermoset or cured polymer refers to a high molecular weight polymer formed by esterification of a polyol and a diacid and further crosslinked by heating, photocuring, microwave curing, infrared curing and the like. Condensation oligomers and polymers of a polyol and a diacid may also be characterized by the acid number (a measure of the number of carboxylic acid groups) and hydroxyl number (a measure of the number of hydroxyl groups). Acid number refers to mass of potassium hydroxide (KOH) in milligrams that is required to neutralize one gram of condensation polymer or oligomer. Hydroxyl number refers to number of milligrams of potassium hydroxide required to neutralize the acetic acid taken up on acetylation of one gram of condensation polymer or oligomer. Condensation oligomers useful in the invention typically have an acid number between about 50 mg/g and about 100 mg/g, about 55 mg/g and about 85 mg/g, about 55 mg/g and about 75 mg/g, or about 55 mg/g and about 65 mg/g; condensation polymers useful in the invention typically have an acid number between about 5 mg/g and about 55 mg/g, about 15 mg/g and about 50 mg/g, about 20 mg/g and about 50 mg/g, or about 35 mg/g and about 50 mg/g.

In some embodiments the polyol component may be glycol, glycerol, erythritol, threitol, arabitol, xylitol, mannitol, sorbitol, maltitol, or combinations thereof. In some embodiments the diacid may be sebacic acid, malonic acid, succinic acid, glutaric acid (5 carbons), adipic acid (6 carbons) pimelic acid (7 carbons), suberic acid (8 carbons), and azelaic acid (9 carbons). Exemplary long chain diacids include diacids having more than 10, more than 15, more than 20, and more than 25 carbon atoms. Non-aliphatic diacids may be used. For example, versions of the above diacids having one or more double bonds may be employed to produce glycerol-diacid co-polymers. Amines and aromatic groups may also be incorporated into the carbon chain. Exemplary aromatic diacids include terephthalic acid and carboxyphenoxypropane. The diacids may also include substituents as well. Reactive groups like amine and hydroxyl may increase the number of sites available for cross-linking. Amino acids and other biomolecules may modify the biological properties of the polymer. Aromatic groups, aliphatic groups, and halogen atoms may modify the inter-chain interactions within the polymer. Any condensation polymer formed from of any of the above listed or other polyols and any of the above listed or other diacids may be included in compositions of the invention.

Examples of poly(polyol sebacate)s for use in the present invention include, but are not limited to, one or more of the following: poly(glycol-sebacate), poly(glycerol-sebacate), poly(erythritol-sebacate), poly(threitol-sebacate), poly(arabitol-sebacate), poly(xylitol-sebacate), poly(mannitol-sebacate), poly(sorbitol-sebacate), poly(maltitol-sebacate), and combinations thereof. In certain embodiments the poly (polyol-sebacate) is poly(glycerol-sebacate).

Examples of oligo(polyol-sebacate)s for use in the present invention include, but are not limited to, one or more of the following: oligo(glycol-sebacate), oligo(glycerol-sebacate), oligo(erythritol-sebacate), oligo(threitol-sebacate), oligo (arabitol-sebacate), oligo(xylitol-sebacate), oligo(mannitol-sebacate), oligo(sorbitol-sebacate), oligo(maltitol-sebacate), and combinations thereof. In certain embodiments the oligo (polyol-sebacate) is oligo(glycerol-sebacate).

While OGS and PGS are described throughout as exemplary condensation oligomers and polymers, it is contemplated that any condensation oligomer or polymer may be used or substituted depending upon the needs of the artisan.

With respect to the mole ratio of polyol monomer to diacid monomer in a condensation polymer used in the present invention, such a mole ratio is typically about 1:1, though other ratios are within the scope of the invention. In some embodiments, the mole ratio of polyol monomer to diacid monomer can be about 1:0.8, about 1:1, about 1:1.2, about 1:1.5, about 1:2, about 1.3, about 1:4, or about 2:3.

In some embodiments, the compositions 12 of the present invention include condensation polymer to condensation oligomer in a weight ratio of polymer:oligomer that is about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10.

In some embodiments, the composition 12 may be manipulated based on the advancement of glycerol sebacic acid esterification of OGS and/or PGS. For instance, depending on the degree of OGS polymerization, OGS may act as a surfactant, wetting agent, functionalized carrier, flow and leveling agent, diluent, plasticizer, resin stabilizer, or specialized processing aid. Additionally, depending on the degree of polymerization of PGS the polymer may be prepared as a gel, elastomer, resin thermoplastic or resin thermoset. Advancement of esterification is determined by measurement of acid number and hydroxyl numbers calculated by those skilled in the art.

In some embodiments, a combination of condensation polymer and condensation oligomer is used in bio-ink compositions of the present invention. A condensation polymer typically has an acid number in a range of from about 35 mg/g to about 50 mg/g and in some embodiments is about 30 mg/g, about 35 mg/g, about 40 mg/g, about 45 mg/g, about 50 mg/g, or about 55 mg/g. A condensation oligomer typically has an acid number in a range of from about 55 mg/g to about 65 mg/g and in some embodiments is about 50 mg/g, about 55 mg/g, about 60 mg/g, about 65 mg/g, or about 70 mg/g.

In some embodiments the condensation polymer and/or condensation oligomer are functionalized. Examples of functional groups include, but are not limited to, acrylate, peptides, cinnamate.

In some embodiments, the condensation polymers or oligomers, such as glycerol-sebacic acid ester resins, may have one or more functional groups that may be "tuned" for hydrophilicity and, in contrast, hydrophobicity. That is, the condensation polymer and/or oligomer may be chosen such that any functional groups modifying the structure impart a desired hydrophilicity or hydrophobicity to the polymerized resin. Therefore it is possible to create custom functionalized resins based on free hydroxyl and free carboxyl chemistries. Such tuning provides for modification of the composition such that the polypeptide loading can be maximized in the aqueous dispersion.

It is further an advantage of tunability to maximize high solids of a fully bioresorbable polymeric structure through the balance of hydrophilicity and hydrophobicity.

In one embodiment, the composition of the present invention includes one or more polypeptides, such as collagen and gelatin. Gelatin or equivalent collagen can be derived from, for example, human, Piscean, jellyfish, porcine, equine or bovine. In a like manner, collagen can be substituted with gelatin A or B. In some embodiments, collagen Type 1, Type 2, Type 3, Type 4, Type 5, Type 6, Type 7, Type 8, Type 9, Type 10, Type 11, Type 12, Type 13, Type 14, Type 15, Type 16, Type 17, Type 18, Type 19, Type 20, Type 21, Type 22, Type 23, Type 24, Type 25, Type 26, or Type 27 may be used. In some embodiments dispersing a polypeptide in water before the addition of a poly(polyol sebacate) or oligo(polyol sebacate) may enhance the dispersion of the poly(polyol sebacate) or oligo(polyol sebacate) in solution. In some embodiments of composition 12, inclusion of a polypeptide may cause the extruded composition to set more rapidly than a composition that does not include a polypeptide.

A polypeptide may be included in compositions of the invention, though any biologically active tissue, and in particular connective tissue can be used. In some embodiments a polyurethane can be included in the place of a polypeptide.

In some embodiments compositions of the present invention further include a bioactive material. Such a bioactive material can be vitamin, such as vitamin E or C, for example, mineral, and/or include tocopherol, ascorbate, retinoic acid, or combinations thereof. Alternatively, the bioactive material can be cells, such as stem cells, progenitor cells, mesenchymal cells, trophic cells, somatic cells, or combinations thereof. In other embodiments, the bioactive material may be biologically active short peptide sequences, growth factors, proteoglycans, glycoproteins, glycosaminoglycans and polysaccharides, nutrients, cytokines, hormones, angiogenic factors, immunomodulatory factors, drugs, or combinations thereof.

In other embodiments, the bioactive material can be selected from growth or morphogenic factors, such as, for example, transforming growth factor, insulin-like growth factor 1, platelet-derived growth factor, bone morphogenetic proteins (bmps); cytokines, such as, for example, interleukins, chemokines, macrophage chemoattractant factors, cytokine-induced neutrophil chemoattractants (gro-1), integral membrane proteins such as integrins and growth factor receptors; membrane associated factors that promote growth and morphogenesis, such as, for example, repulsive guidance molecules; cell attachment or adhesion proteins, such as, for example, fibronectin and chondronectin; hormones, such as, for example, growth hormone, insulin and thyroxine; pericellular matrix molecules, such as agrin, laminin, thrombospondin, tenascin, veriscan, perlecan, syndecan, small leucine-rich proteoglycans and fibromodulin; nutrients, such as, for example, glucose and glucosamine; nucleic acids, such as, for example, RNA and DNA; anti-neoplastic agents, such as, for example, methotrexate and aminopterin; anti-inflammatory agents, such as, for example, naproxen sodium, salicylic acid, diclofenac and ibuprofen; enzymes, such as, for example, phosphorylase, sulfatase and kinase; and metabolic inhibitors, such as, for example, RNAi, cycloheximide and steroids.

In some embodiments, compositions of the present invention include a fatty acid. Such a fatty acid may be admixed with the poly(polyol-sebacate), oligo(polyol-sebacate) and polypeptide components, or in some embodiments the fatty acid is co-esterified with polymeric polyol-sebacate or oligomeric polyol sebacate. Fatty acids for use with the invention include, but are not limited to, eicosapentaenoic acid, docosahexaenoic acid, arachidic acid, gadoleic acid, arachidonic acid, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, cerotic acid, myristoleic acid, sapienic acid, elaidic acid, vaccenic acid, linoeladic acid, and combinations thereof.

Compositions 12 of the invention may comprise various aqueous dispersible combinations of (glycerol-sebacate) esters combined with gelatin or collagen or other suitable extracellular matrix (ECM) connective tissue polypeptide, polysaccharide and combinations thereof, and optionally including other physiological acceptable biomaterials and solvents at a low temperature (less than about 40° C.). These compositions may be useful in building 3-D scaffolds for tissue engineered constructs by extrusion, printing, and molding.

Any suitable method of forming a condensation reaction product of a polyol and a diacid may be employed for producing the ester component of the composition 12. One particularly suitable method is the process described in U.S. application Ser. No. 14/725,654 filed May 29, 2015 which is hereby incorporated by reference in its entirety.

One method of producing the composition 12, in some embodiments, comprises adding a solid polypeptide flour (e.g., gelatin or collagen) to warm or room temperature water and dispersing under mixing to form a polypeptide hydrogel and adding solid or molten ester to the polypeptide hydrogel dispersion under mixing to form an ester/polypeptide hydrogel; mixing the ester/polypeptide hydrogel under low heat; and cooling the ester/polypeptide composition. The polypeptide hydrogel formed may be a viscous fluid dispersion. In some embodiments the warm water may be at a temperature of about 25° C. to about 85° C., or about 25° C. to about 75° C. or about 25° C. to about 65° C. or about 30° C. to about 55° C. or about 35° C. to about 50° C. or about 40° C. to about 45° C. In some embodiments the low heat may be a temperature of about 25° C. to about 150° C., about 40° C. to about 135° C., about 55° C. to about 120° C., or about 70° C. to about 115° C. In some embodiments the low heat may be a temperature of about 25° C. to about 40° C., about 40° C. to about 75° C., about 75° C. to about 100° C., about 100° C. to about 115° C., or about 100° C. to about 125° C. The ester/polypeptide hydrogel is stable (i.e. does not separate) and in some embodiments liquefies at a temperature at or below about 40° C., or in a range of about 35° C. and about 40° C., or in a range of about 38° C. to about 40° C. Upon cooling the composition solidifies at room temperature into a composition having a soft texture that is somewhat similar to that of cheesecake. Despite the original aqueous temperature used to dissolve the polypeptide, the composition may be able to flow at temperatures about or below 40° C.

Typically, low shear mixing is used to combine the components in composition 12. In some embodiments, shear blade, lightning mixer, or other high shear mixing can be used to disperse a higher ratio of polypeptide and ester (e.g. glycerol-sebacic acid ester) into the water.

The method and order of mixing is aids in obtaining or avoiding certain properties which might be desirable depending upon application. Polypeptide hydration in water should be consistently carried out as the initial step followed by adding the ester in molten form to the hydrated mixture to achieve proper distribution throughout the solution.

In another embodiment, a method of producing a composition comprises modifying polarity of low molecular weight glycerol-sebacic acid ester via degree of polymerization for aqueous dispersibility based on hydrophilicity and hydroxyl functionality. This approach may vary the order of added components according to formulation needs. For example, in one embodiment a method of producing composition 12 may include adding a solid polypeptide flour (gelatin or collagen) to warm water and dispersing under mixing power to form a polypeptide hydrogel; adding OGS to the polypeptide hydrogel and dispersing under mixing power to form an OGS/polypeptide hydrogel; and adding PGS to the OGS/polypeptide hydrogel dispersion under mixing power to form a PGS/OGS/polypeptide hydrogel; mixing the PGS/OGS/polypeptide hydrogel under low heat; and cooling the PGS/OGS/polypeptide composition.

In addition the polarity of PGS and OGS may be further modified by co-esterification with an omega-# fatty acid. This modification would decrease the polarity of the resulting composition by the addition of non-polar alkyl chains.

3-D structures of the invention upon extrudation and cooling, but before processing to induce cross-linking (i.e., A-stage) may have a consistency similar to cheesecake that is rigid but spongy and generally capable of returning to its original shape after slight deformation. Depending on the ratio of polypeptide/PGS in the composition used to form the 3-D structure, the viscosity and tackiness may vary, with viscosity decreasing and tackiness increasing with increased PGS. The tackiness may increase as the ratio of OGS:gelatin or the ratio of PGS:gelatin or the ratio of (OGS and PGS):gelatin increases.

Composition 12 may be printed as an A-staged composition and further advanced to B-stage, in which the cross-linking has been induced within and between the deposited layers of composition 12. In one embodiment, an A-staged composition may be advanced to B-stage by condensation polymerization. Composition 12 may be delivered in multiple layers in the X-Y plane at some predetermined vertical angle in an ink jet like printing apparatus or similar device providing spatial deposition. The deposition in-plane is repeated such that the sequential compilation of planes builds a 3-D construct of interest. A method for forming a three-dimensional scaffold may include extruding a first two-dimensional layer of a bio-ink composition onto a substrate, and building a second two-dimensional layer of a bio-ink composition upon the first two-dimensional layer in a third dimension, wherein the bio-ink composition comprises a polymeric glycerol-sebacate and a polypeptide.

One of the features of this invention is that the glycerol-sebacic acid esters/polypeptide composition provides a biopolymer scaffold material capable of being extruded through the print head at physiological temperatures. This feature further allows the direct incorporation of bioactive components including biologics, trophic agents and cells (i.e. stem, progenitor, mesychencimal, or somatic). The temperature at which compositions can be processed through a nozzle may provide another advantage over lactide and glycolide compositions. The 3-D print head nozzle temperature of a typical lactide or glycolide as an extrudate is 150° C. to 250° C. These temperatures may make it impossible to incorporate cells or biologics into lactide and glycolide compositions for simultaneous biopolymer/cell extrudates useful in 3-D scaffold printing. The poly(glycerol-sebacate)/polypeptide composition of the composition 12 may be extruded through a 3-D print head nozzle at physiological temperatures (i.e. about 37° C. to about 40° C.). As compared to typical polymer extrusion temperatures (e.g. 150° C. to 250° C.), being able to extrude the composition 12 at physiological temperatures allows inclusion of bioactive materials, which typically biodegrade at temperatures greater than about 40° C. to 50° C. The bio-ink composition may be extruded at a temperature at or below about 40° C., or in a range of about 35° C. and about 40° C., or in a range of about 38° C. to about 40° C.

A further benefit of the composition 12 is the rapid solidification of the bioelastomer biodegradable polymer extrudate allowing for three-dimensional additive buildup of structures as well as rapid processing of molds.

Methods of forming a 3-D structure may further include a step of heating the three-dimensional scaffold. A heating step may induce cross-linking between and among the layers of the bio-ink composition, causing the 3-D scaffold to "set". Typically, the three-dimensional structure is heated to a temperature in the range of about 30° C. to about 120° C., such as about 30° C., about 40° C., about 50° C., about 60° C., about 70° C., about 80° C., about 90° C., about 100° C., about 110° C., about 120° C. or any temperature, range or sub-range between any of the foregoing.

Methods of forming a 3-D structure may further include a step of photocuring the bio-ink composition. In one embodiment, the A-stage glycerol-sebacic acid esters may be acrylated to create a free radical photocurable extrudate. In this composition, the scaffold may be engineered in 3-D and "photo-set" in the A-stage before processing in the B-stage. This can enhance handling and storage.

The A-stage composition may be epoxidized to create a cationic photocureable extrudate. In this composition the scaffold can be engineered in 3-D and "photo-set" in the A-stage before processing in the B-stage. This can enhance handling and storage.

The A-stage composition may include a free co-blended fatty acid like the omega-# fatty acids wherein the 3-D structure can be air-cured for post print setting.

In other embodiments such as molding and extrusion the entire structure can be processed with IR curing, acetone wash, lyphophilization, etc.

Furthermore, any structures formed of the compositions described herein can be air dried. They may then be rehydrated as desired and, if uncured, may expand to greater than their original size, although cured, crosslinked structures return to their original shape and size.

As noted previously, in some embodiments, the PGS and OGS may be further co-esterified with omega-# fatty acid. Compositions containing the omega-series may be air cured at room temperature (e.g., about 25° C.), or slightly elevated temperature, for example, at about 30° C., about 35° C., about 40° C., about 45° C., or about 50° C.

The OGS/PGS/polypeptide/water compositions may be formulated with biocompatible organic and inorganic materials with high dipole moments and microwave cured. In some such embodiments the PGS may serve as a material having a high dipole moment depending on the number of free hydroxyls and carbonyl groups present. In some embodiments a material with a high dipole moment is admixed as part of the bio-ink composition 12. In other embodiments the PGS is functionalized with a moiety having a high dipole moment. Typical high dipole moment materials include glycerol, polyethylene glycol (PEG) and other materials having carbonyl or hydroxy groups.

Figure 2:
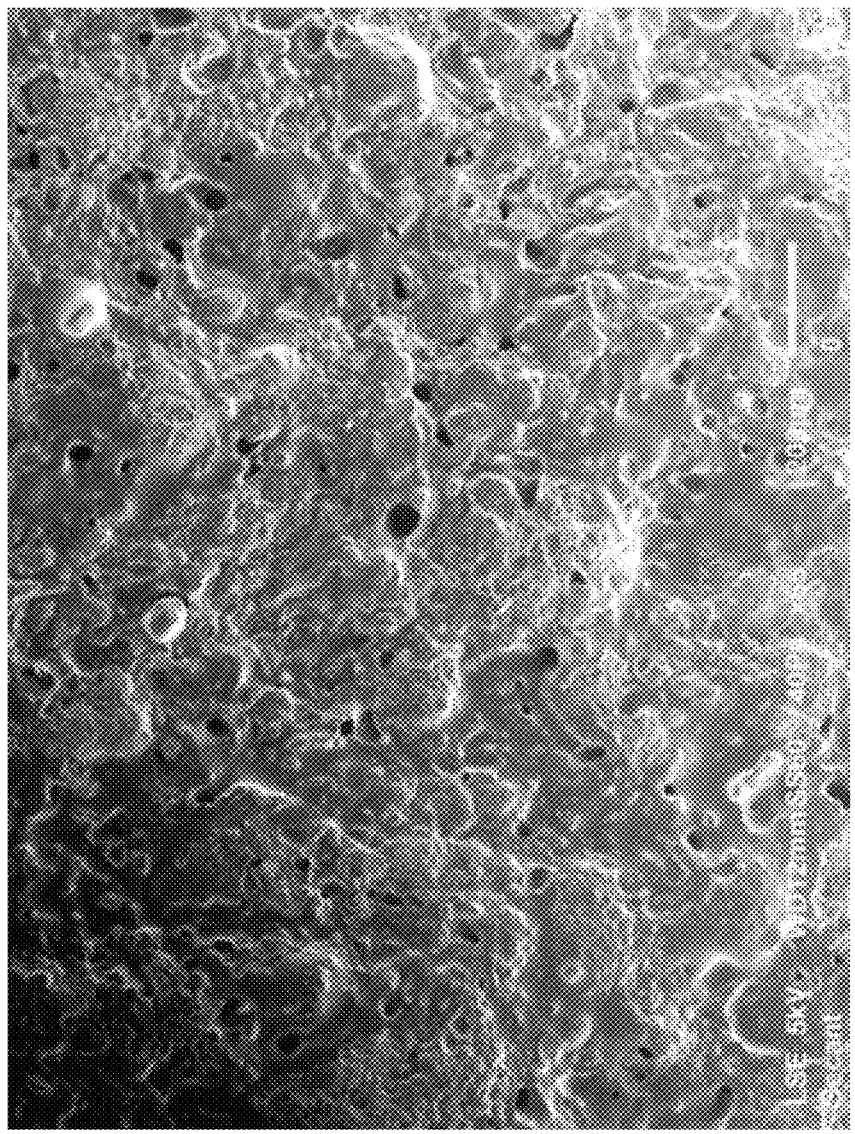
FIG. 2 is a lyophilized SEM of an enlarged cross sectional view of a 3-D printed structure in accordance with an exemplary embodiment.

An unexpected desirable benefit of the aqueous phase is that the water behaves like a porogen when the 3-D structure is dehydrated from the finished construct. This provides porosity to the 3-D construct upon aqueous evacuation of said 3-D composition. In one embodiment, water may be removed from the 3-D structure through lyophilization, as seen in FIG. 2. Typically, the 3-D structure is lyophilized at a temperature of about 0° C. to about −160° C., about −20° C. to about −140° C., about −40° C. to about −120° C., or about −60° C. to about −100° C. In some embodiments the three-dimensional structure may be lyophilized at a temperature of about 0° C., about −10° C., about −20° C., about −30° C., about −40° C., about −50° C., about −60° C., about −70° C., about −75° C., about −80° C. about −85° C., about −90° C., about −100° C., about −110° C., about −120° C., about −130° C., about −140° C., about −150° C., or about −160° C. Thus, traditional porogens, such as sodium chloride, which can lead to pocking or scarring of the material and can leave salt in the structure, even after washing, are not required.

The average pore size of the 3-D object 10 may be in the range of about 5 μm to about 80 μm, about 10 μm to about 70 μm, about 20 μm to about 60 μm, or about 30 μm to about 50 μm. In some embodiments the average pore size after dehydration is less than about 30 μm, less than about 25 μm, or less than about 20 μm. In some embodiments the average pore size is about the size of or smaller than white blood cells. In some embodiments the average pore size is small enough to prevent macrophages to enter the pores.

Another unexpected benefit of this composition is the uniformity of polypeptide fibrous network that can support and reinforce said ester polymer structure. For scaffold constructs, collagen may be an important extracellular matrix (ECM) component. The composition 12 may provide for a uniform dispersion of collagen and like-polypeptide derivatives to be uniformly dispersed.

In some cases, compositions in accordance with exemplary embodiments may be printed directly on a material to provide a PGS coating on the material. Such coatings may impart beneficial properties to the substrate material, such as increased tensile strength of a woven textile. In some embodiments, the substrate material to be coated is a polymer. Typical polymers may include polyether ether ketone (PEEK), polyglycolic acid (PGA), polylactic acid (PLA), poly lactic-co-glycolic acid (PLGA), polyethylene terephthalate (PET), polypropylene (PP), and combinations thereof.

Returning to FIG. 1, the 3-D printer assembly 100 includes the print head 14 having the nozzle 16 and the reservoir 18 for holding composition 12 and is further shown as comprising a heating element 20. Printer assembly 100 may further comprise a scanner 28 for scanning an object and/or a computer aided design program for designing the object.

The heating element 20 can be employed to precisely aid in the rheological properties of the composition 12 for physiological temperature control.

Referring to FIGS. 6A-6D, and FIGS. 7A-7C, the heating element 20 may include a bore 40 for receiving the nozzle 16. The heating element 20 may further include an opening 42, which may extend from the outer surface of the housing element and opens into bore 40. Opening 42 may receive a set screw (not shown) and is configured to allow the set screw to be in communication with the nozzle 16. Heating element 20 may include a bore 44 for receiving a heater cartridge (not shown). Opening 46 extends from the outer surface of the housing element to bore 44 for receiving a set screw (not shown) and is configured to allow the set screw to be in communication with heater cartridge. Heating element 20 may include a bore 48 for receiving a thermocouple.

The heating element 20 may be matched to the composition 12 so that the composition is heated to the desired temperature. The heating element 20 may also be configured to allow for higher percent solids to be extruded by allowing slight material flow, between 25-40° C.

In some embodiments heating element 20 has different zones to allow for cooling one or more reservoirs while heating one or more other reservoirs.

The build platform 24 may be temperature controlled. In one embodiment, the temperature may be maintained at less than about 25° C., as opposed to a hot build platform, which is normally set to the material's glass transition temperature. The cooled platform 24 may allow elevated flow levels and ensure rapid set up of extruded build material. In some embodiments, the platform 24 is cooled to a temperature range of about 0° C. to about 25° C., about 0° C. to about 10° C., about 5° C. to about 15° C., about 10° C. to about 20° C., or about 15° C. to about 25° C. The cooled platform 24 may mimic placing the substrate and/or 3-D structure in a refrigerator for a faster set time.

Referring to FIGS. 1, 4, 5, and 7, nozzle 16 may be designed to allow a bio-ink composition 12 to be extruded through cold extrusion, via a syringe and plunger system, material reservoir and pneumatic system or other extrusion.

Referring to FIGS. 4A-4E, the nozzle 16 may include a tip 30. The nozzle 16 may include a feed line 36 for a second material, such as a fiber core. Accordingly, the nozzle 16 may be configured to create a sheath-core extrudate wherein the ink composition may surround the fiber core. Typical fibers include collagen, polyglycolic acid (PGA), polycaprolactone (PCL), polylactic acid (PLA) and any other bioresorbable fiber configured to add additional structure and strength to the final print. The fiber core may be at a temperature cooler than that of the polymeric bio-ink composition. Typically, the fiber core may be cooled to a temperature of about 25° C., about 30° C., about 35° C., or about 40° C., about 25° C. to about 40° C., about 25° C. to about 35° C., or about 25° C. to about 30° C. In some embodiments, the fiber core may be cooled to a temperature of about 5° C., about 10° C., about 15° C., about 20° C., or about 25° C. less than composition 12. Referring to FIG. 4E, in some embodiments the nozzle may further comprise a reservoir connector element 19, as well a pitch associated with the bore of the nozzle to that allow for the mixing of composition 12 as it is being extruded.

Currently, standard art ignores the fill pattern of the three dimensional builds. Infill density can be manipulated in current practice to affect the weight and amount of material used, caring solely for the external architecture. Bioprinting has incorporated pores or other internal structures designed into the three dimensional print, essentially printing at a 100% infill. The proposed invention also manipulates the internal architecture of the build, providing layer by layer pattern formulation. Incorporated with the fiber core, the build will exhibit different properties based on the pattern and layering of the sheath core.

Referring to FIGS. 5A and 5B, an embodiment of the nozzle may have multiple feeds 36 to the tip 30 such that a single nozzle may mono-co- or multi-extrude compositions on demand; such feeds 36 may be positioned in different arrangements according to the needs of the artisan. FIGS. 5A and 5B depict a nozzle having 3 feeds, which is typical, but a nozzle having any number of feeds, such as one, two, three, four, five or more is included within the scope of the invention. Each feed may be connected to a reservoir for holding the composition 12 or a component to be added to the composition 12. One or more feeds may be temperature controlled. For example, the composition 12 may be heated to a first temperature and a feed having a biologic may be maintained at a second temperature lower than the first temperature. Referring to FIG. 5C, an embodiment may have multiple reservoirs 18 that lead to a single feed 36. The multiple reservoirs would then be mixed through the bore as described previously with respect to FIG. 4E.

The present invention provides for the design of a nozzle configuration wherein the said nozzle has a self-contained heat sink to provide energy sufficient to allow said compositions to flow through said nozzle without harming the living cells. Said nozzle can be designed into a print head having multiple reservoirs 18, each containing a different composition, raw material, agent of growth, cell culture, physiologically acceptable medium, various ECM proteins (e.g., collagen, fibronectin, laminin, elastin, and/or proteoglycans), basic nutrients such as sugars and amino acids, growth factors, antibiotics (to minimize contamination).

The composition 12 may additionally comprise non-cellular materials that provide specific biomechanical properties that enable bioprinting, or growth promoter.

Referring to FIG. 1, the 3-D printer assembly may include one or more computers 26 having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

The construct instructions are delivered via software commands. According to another aspect of this invention the solid filling of the 3-D object is manipulated by customized software.

Referring to FIG. 1, the 3-D print assembly may further include a scanner 28. A scanner may be used to scan a patient's organ, bone, or other anatomy to provide on the size and dimension of the 3-D structure 10 to be constructed using the 3-D print assembly. A typical scanner is a CT scanner, but any scanner capable of scanning the patient's organ, bone, or other anatomy in three dimensions may be used.

EXAMPLES

A composition, Formulation 1, was formed comprising 10% gelatin, 59% water and 31% PGS, all by weight. Mixing was completed with a magnetic stir bar and a temperature controlled hot plate. A control, Control 1, was neat PGS (made at 120° C. for 48 hours under vacuum).

Using an oscillatory rheometer, a reverse temperature sweep is performed on both materials to monitor the changes in the storage modulus (G') as a function of temperature. The test was conducted by holding the composition at 40° C. for 60 seconds and then lowering the temperature to 25° C. and holding for 300 seconds. The results are shown graphically in FIG. 3.

In this example, a G' of ~10 Pa is indicative of a free flowing viscous liquid so at 40° C. both Formulation 1 and the control are behaving as liquids. The Formulation 1 composition experiences a drastic increase in storage modulus after the temperature decreases, while the control's storage modulus remains constant. The increase in G' indicates the Formulation 1 composition is solidifying and becoming more solid-like in morphology, resulting in a material suitable as a bio-ink.

Figure 3:
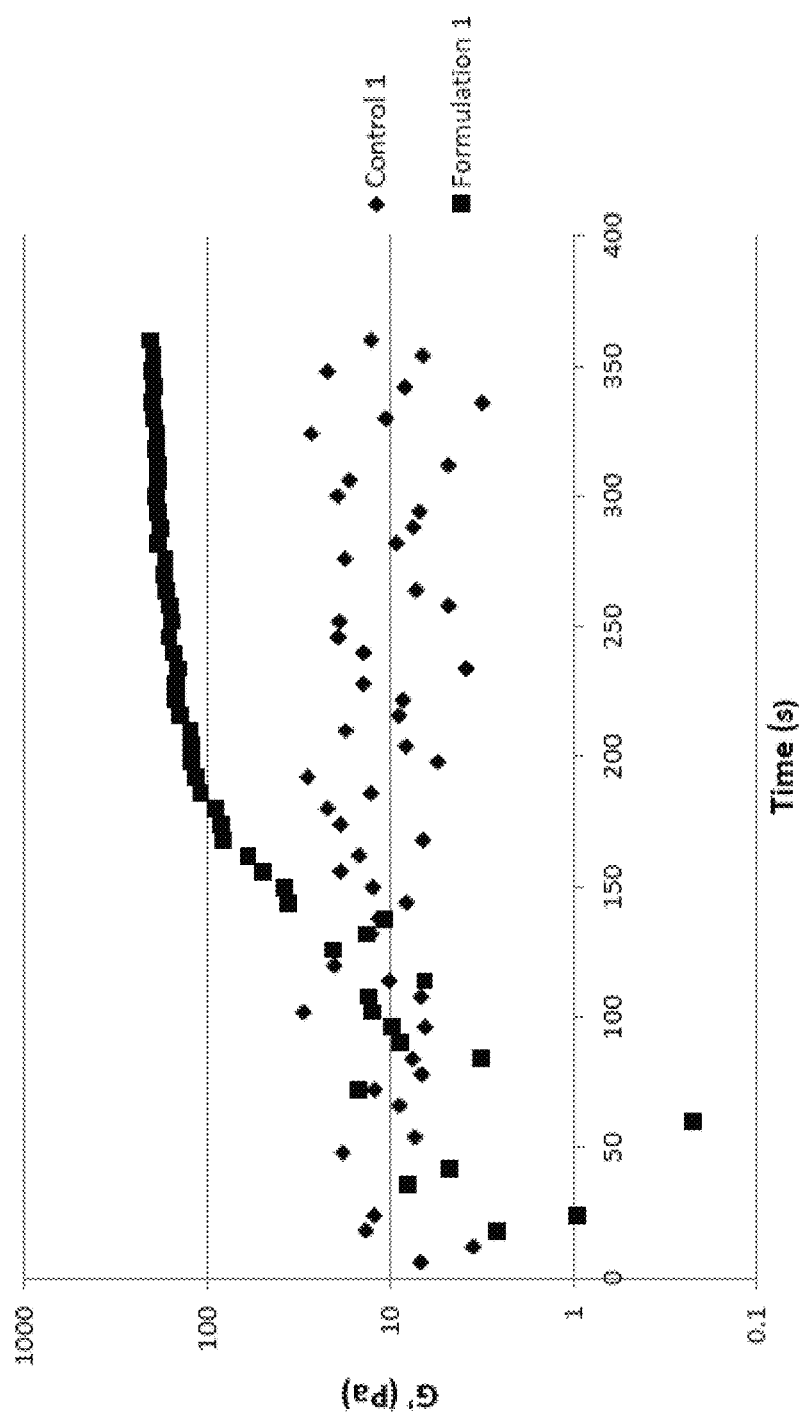
FIG. 3 is a temperature sweep curve comparing a control solution to a composition in accordance with an exemplary embodiment.
Figure 6C:
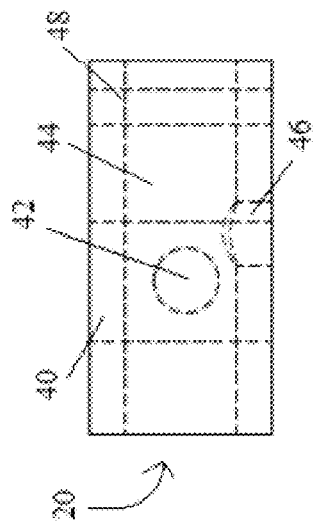
FIG. 6C is a front elevation view of the heating element shown in FIG. 6A.
Figure 6D:
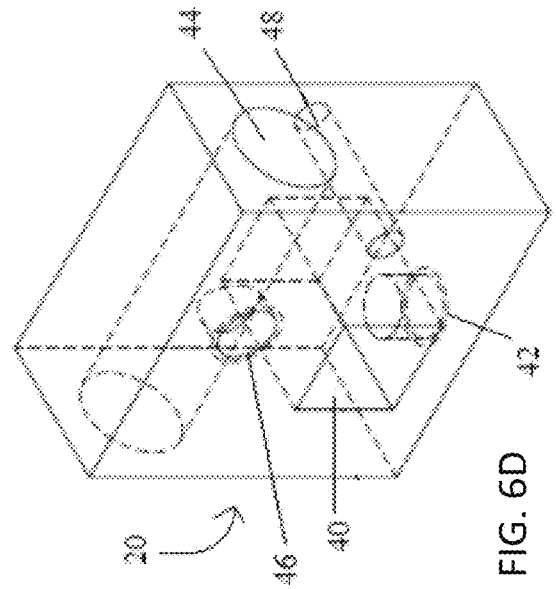
FIG. 6D is a perspective view of the heating element shown in FIG. 6A.
Figure 6A:
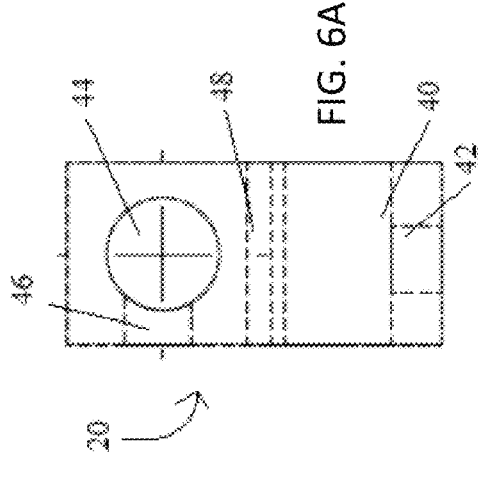
FIG. 6A is a side elevation view of a heating element according to an exemplary embodiment of the invention.
Figure 6B:
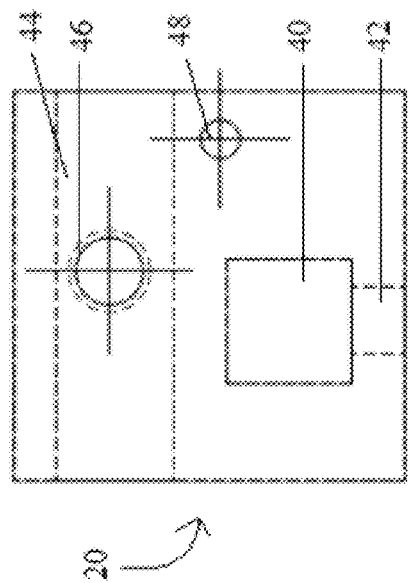
FIG. 6B is a bottom elevational view of the heating element shown in FIG. 6A.
Figure 8B:
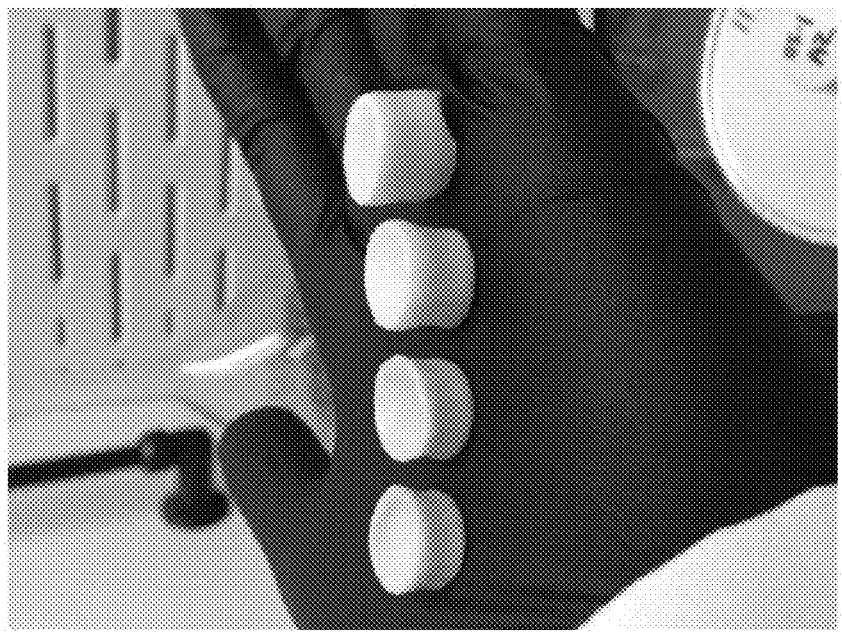
FIG. 8B illustrates homogeneity in dehydrated, formed structures and the impact of PGS concentration on the aspect ratio when mixing steps during production are carried out in a different order.
Figure 8A:
FIG. 8A illustrates inhomogeneity in dehydrated, formed structures that can result when mixing steps during production are carried out in one order.

In FIG. 3, the control continues to flow even after dropping the temperature from 40 to 25° C. The composition of Formulation 1, on the other hand, flows at 40° C. and then levels off completely after 100 seconds at 25° C. The inconsistencies seen at 40° C. for both the control and the Formulation 1, as well as the fluctuations of the control held at 25° C. are indicative of the parallel plate torque detection at or below the detection limit due to the low viscosity of the materials.

Since the control keeps this inconsistency throughout the test, it can be assumed the 15° C. temperature decrease has no effect on the flow of the control. A gel modifier, like gelatin or collagen, such as is used in Formulation 1, provides an ability to extrude the PGS containing composition and quickens the solidification process.

A composition of Formulation 2 was made of 13% gelatin, 74% water and 13% PGS by weight. A composition of Formulation 3 was made of 11.5% gelatin, 65.5% water and 23% PGS by weight. Formulation 4 was made of 10% gelatin, 59% water and 31% PGS by weight and Formulation 5 was 9.5% gelatin, 53% water and 37.5% PGS by weight. Each of the compositions in these four examples were formulated with PGS made at 130° C. for 25 hours under vacuum.

Figure 12:
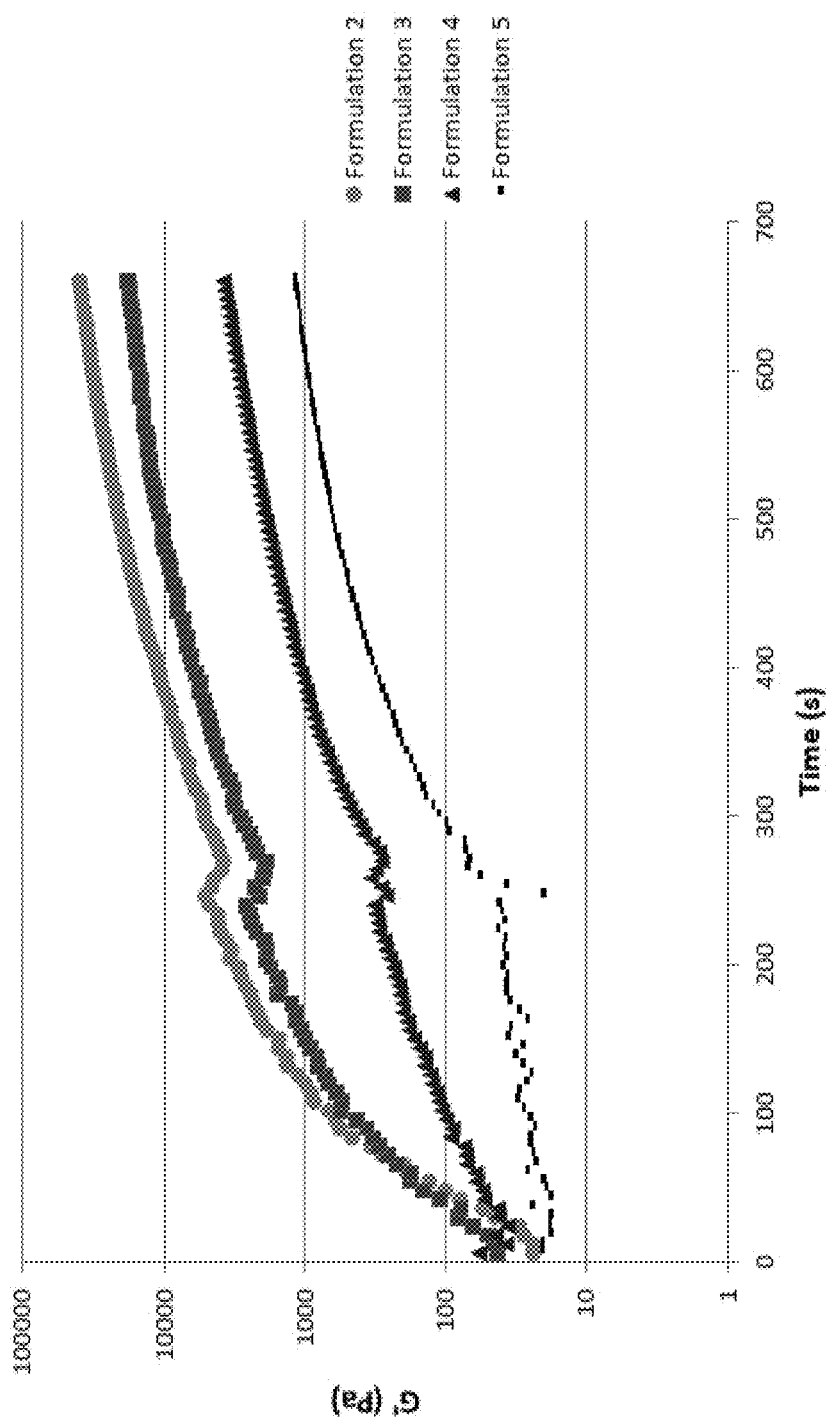
FIG. 12 demonstrates the rheology and the impact glycerol-sebacic acid ester concentration has on the storage modulus of compositions in accordance with exemplary embodiments.

FIG. 12 shows several embodiments tested using similar methodology as described in FIG. 3, except that the materials were held at 40° C. for 240 seconds and 25° C. for 420 seconds. All four samples show the same characteristic solidification as described previously in FIG. 3 and the degree of solidification is tunable based on the level of PGS present in the formulation. The storage modulus increases (higher degree of solidification) with decreasing PGS concentration. Formulation 5 shows a preferred embodiment having rapid set time from a liquid phase to a solid phase, whereas Formulations 1-4 did not demonstrate a liquid phase.

Figure 9A:
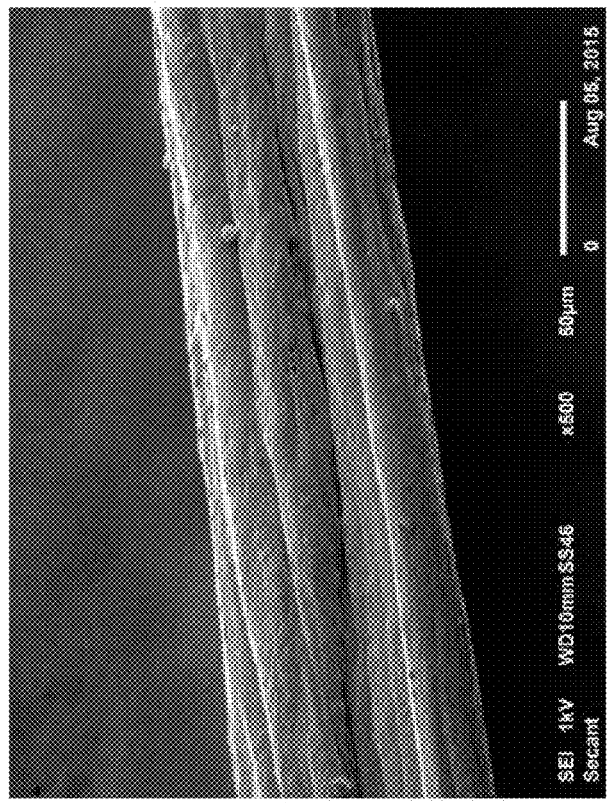
FIG. 9A is a collagen fiber shown at a magnification of ×500.
Figure 9B:
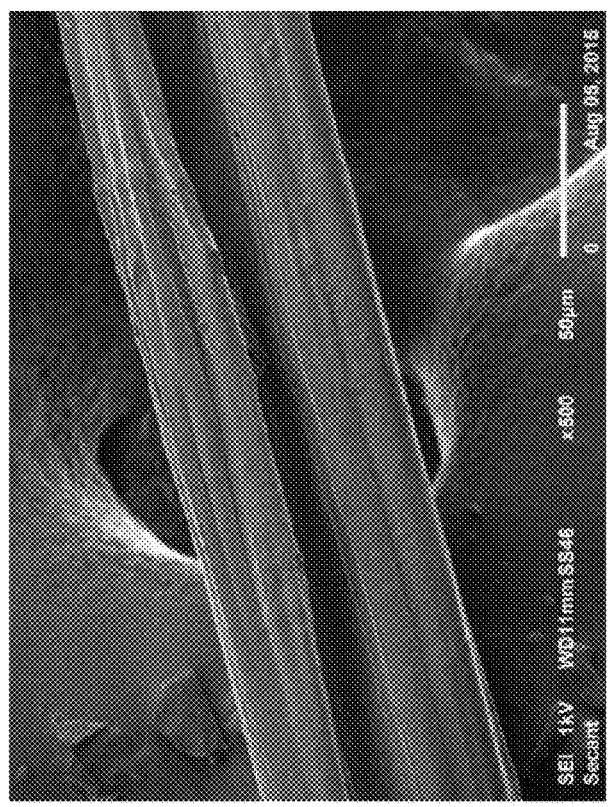
FIG. 9B is a 45 μm fiber of a composition in accordance with an exemplary embodiment of the present invention shown at a magnification of ×500.

In another example, a formulation was created to demonstrate the flexibility to be formed through an extrusion process. A 0.6% collagen, 49.4% water and 50% PGS w/w formulation was extruded through a 480 µm orifice into an acetone processing bath. The striations of a pure collagen fiber (FIG. 9A) are similar to the striations seen in the example (FIG. 9B) indicating the microstructure is similar. This process is capable of creating fibers with measurable tenacity.

Figure 10:
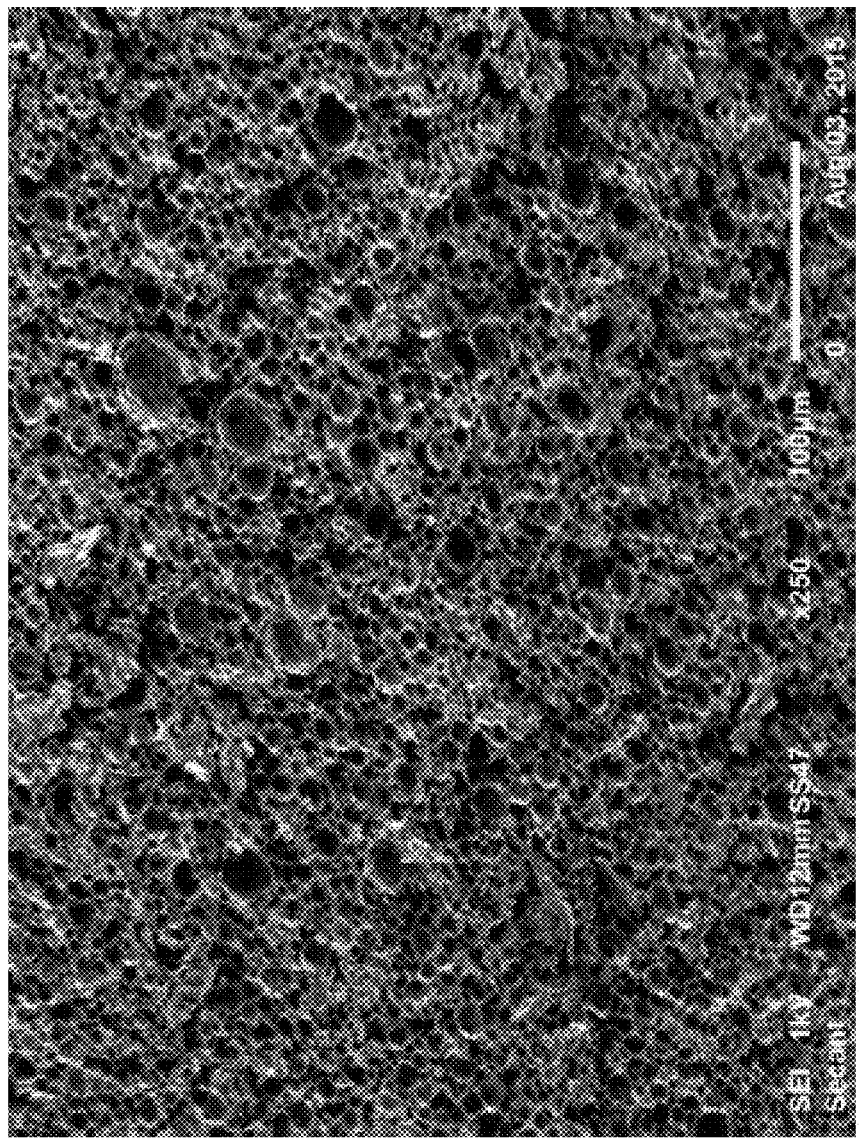
FIG. 10 is a thermally crosslinked and processed composition in accordance with an exemplary embodiment showing consistent porosity across its cross section and shown at a magnification of ×250.

In another example, the benefit of using low molecular weight ester as a modifier was demonstrated in the creation of a porous construct. A formulation of 9.5% gelatin, 53% water, 18.75% low MW glycerol-sebacic acid ester (OGS), and 18.75% high MW glycerol-sebacic acid ester (PGS) was dehydrated in a processing bath and then thermally cross-linked for 72 hours at 30° C. under vacuum. FIG. 10 is a cross sectional SEM image of the resulting product and reveals a highly porous network with pores less than 50 µm. Without being bound by a specific theory, it is believed that the OGS acts as a porogen due to the increased solubility of the material in acetone.

Figure 11B:
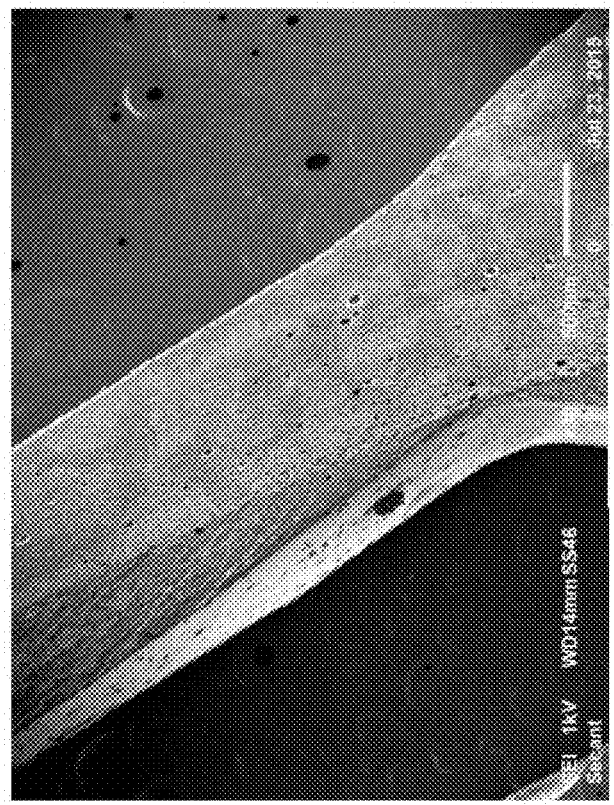
FIG. 11B is a formed dehydrated composition in accordance with an exemplary embodiment in which the order of addition of mixing results in a uniform distribution thereby creating a porous network.
Figure 11A:
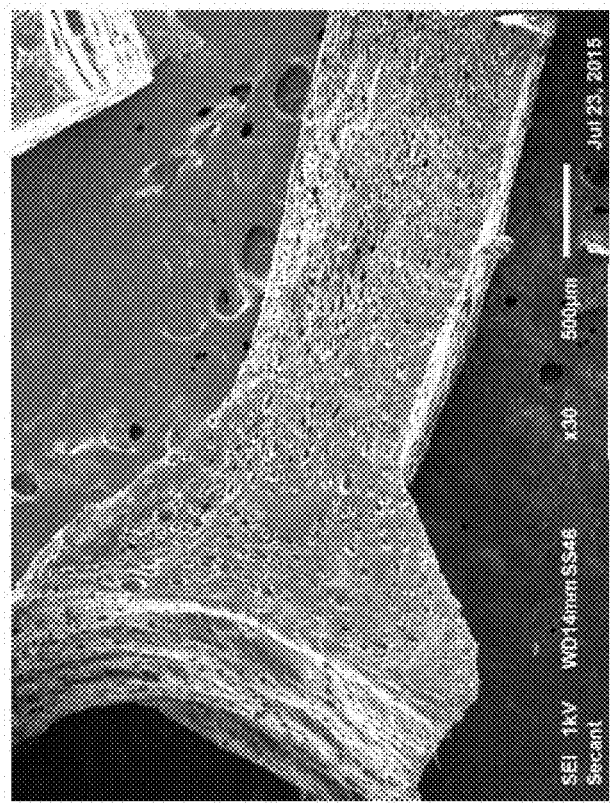
FIG. 11A is a formed dehydrated composition in accordance with an exemplary embodiment in which the order of addition of mixing results in large pockets of glycerol-sebacic acid esters.

Compositions of Formulation 2 were formed by varying the order of mixing. In one example, shear mixing of water, gelatin and molten PGS was performed. In another example, shear mixing of gelatin added to warmed water was performed and then shear mixing of the water/gelatin mixture and molten PGS was performed. The compositions were then molded and dehydrated and the results are shown in FIGS. 11A and 11B, respectively. FIG. 11A contains clear pockets of PGS that are not evenly distributed, while FIG. 11B is evenly distributed with uniform porosity.

Another embodiment of the current invention is the ability to load therapeutic additives to the polymer/polypeptide composition. A composition similar to Formulation 4 was made consisting of 9.5% gelatin, 53% water, 28% PGS and 9.5% hydroxyapatite. Elemental mapping showed the homogenous distribution of hydroxyapatite throughout the entire polymer/polypeptide composition.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A composition comprising:
   water;
   an ester of a polyol and a diacid; and
   a polypeptide;
   wherein the composition comprises a uniform aqueous dispersion of the ester and the polypeptide in the water.

2. The composition according to claim 1, wherein the ester comprises a glyercol-sebacic acid ester compound.

3. The composition according to claim 2, wherein the glyercol-sebacic acid ester compound is a polymeric compound having a molecular weight greater than 10,000.

4. The composition according to claim 3, further comprising a glyercol-sebacic acid ester compound having a molecular weight less than 10,000.

5. The composition according to claim 2, wherein the composition comprises:
   about 30% to about 85% by weight water;
   about 10% to about 60% of the glyercol-sebacic acid ester compound; and
   about 0.1% to about 30% polypeptide.

6. The composition according to claim 2, wherein the composition comprises:
   about 40% to about 85% by weight water;
   about 10% to about 50% of the glyercol-sebacic acid ester compound; and
   about 5% to about 30% polypeptide.

7. The composition according to claim 1, wherein the ester is functionalized.

8. The composition according to claim 1, further comprising a bioactive material.

9. The composition of claim 8, wherein the bioactive material is selected from the group consisting of vitamins, minerals, tocopherol, ascorbate, retinoic acid, and combinations thereof.

10. The composition of claim 8, wherein the bioactive material comprises cells.

11. The composition of claim 8, wherein the bioactive material is selected from the group consisting of peptide sequences, growth factors, proteoglycans, glycoproteins, glycosaminoglycans, polysaccharides, nutrients, cytokines, hormones, angiogenic factors, immunomodulatory factors, drugs, and combinations thereof.

12. The composition according to claim 1, further comprising a fatty acid.

13. The composition according to claim 12, wherein the fatty acid is co-esterified with the polyol-diacid ester.

14. The composition according to claim 1, wherein the polypeptide is collagen.

15. The composition according to claim 1, wherein the polypeptide is gelatin.

16. The composition according to claim 1, wherein the composition consists of 8-12% by weight gelatin, 35-40% by weight glyercol-sebacic acid ester compound, and the balance water.

17. The composition according to claim 1, wherein the diacid is sebacic acid.

18. The composition of claim 1, wherein the ester is aqueously dispersible and biodegradable and the polypeptide is a hydrated matrix in the composition.

* * * * *